United States Patent
Mansi et al.

(10) Patent No.: US 11,445,994 B2
(45) Date of Patent: Sep. 20, 2022

(54) NON-INVASIVE ELECTROPHYSIOLOGY MAPPING BASED ON AFFORDABLE ELECTROCARDIOGRAM HARDWARE AND IMAGING

(71) Applicant: Siemens Healthcare GmbH, Erlangen (DE)

(72) Inventors: Tommaso Mansi, Plainsboro, NJ (US); Tiziano Passerini, Plainsboro, NJ (US); Puneet Sharma, Monmouth Junction, NJ (US); Terrence Chen, Princeton, NJ (US); Ahmet Tuysuzoglu, Franklin Park, NJ (US); Shun Miao, Princeton, NJ (US); Alexander Brost, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 253 days.

(21) Appl. No.: 15/878,557

(22) Filed: Jan. 24, 2018

(65) Prior Publication Data
US 2019/0223819 A1 Jul. 25, 2019

(51) Int. Cl.
*A61B 6/00* (2006.01)
*A61B 5/00* (2006.01)
(Continued)

(52) U.S. Cl.
CPC .......... *A61B 6/5247* (2013.01); *A61B 5/0077* (2013.01); *A61B 5/282* (2021.01);
(Continued)

(58) Field of Classification Search
CPC ... A61B 5/0245; A61B 5/6801; A61B 5/6813; A61B 5/04012; A61B 5/0402;
(Continued)

(56) References Cited

U.S. PATENT DOCUMENTS

| 6,354,493 B1 | 3/2002 | Mon |
| 9,463,072 B2 | 10/2016 | Comaniciu et al. |

(Continued)

FOREIGN PATENT DOCUMENTS

CN 107203988 A * 9/2017 ............. G06T 15/10

OTHER PUBLICATIONS

Veisterä H., Lötjönen J. "Reconstructing 3D Boundary Element Heart Models from 2D Biplane Fluoroscopy." In: Katila T., et al., Montagna Functional Imaging and Modeling of the Heart. FIMH 2001. Lecture Notes in Computer Science, vol. 2230. Springer, Berlin, Heidelberg. (Year: 2001).*

(Continued)

*Primary Examiner* — Unsu Jung
*Assistant Examiner* — Adreanne A. Arnold

(57) ABSTRACT

For non-invasive EP mapping, a sparse number of electrodes (e.g., 10 in a typical 12-lead ECG exam setting) are used to generate an EP map without requiring preoperative 3D image data (e.g. MR or CT). An imager (e.g., a depth camera) captures the surface of the patient and may be used to localize electrodes in any positioning on the patient. Two-dimensional (2D) x-rays, which are commonly available, and the surface of the patient are used to segment the heart of the patient. The EP map is then generated from the surface, heart segmentation, and measurements from the electrodes.

19 Claims, 5 Drawing Sheets

(51) Int. Cl.

| | |
|---|---|
| *G06T 17/00* | (2006.01) |
| *G06T 7/10* | (2017.01) |
| *G06T 17/20* | (2006.01) |
| *G06T 15/20* | (2011.01) |
| *G06T 7/00* | (2017.01) |
| *G06N 20/00* | (2019.01) |
| *A61B 6/02* | (2006.01) |
| *A61B 5/282* | (2021.01) |
| *A61B 5/341* | (2021.01) |
| *A61B 5/107* | (2006.01) |
| *A61B 5/319* | (2021.01) |
| *A61B 5/339* | (2021.01) |

(52) U.S. Cl.
CPC ............ *A61B 5/341* (2021.01); *A61B 5/7267* (2013.01); *A61B 5/742* (2013.01); *A61B 6/022* (2013.01); *A61B 6/461* (2013.01); *A61B 6/503* (2013.01); *A61B 6/5205* (2013.01); *G06N 20/00* (2019.01); *G06T 7/0012* (2013.01); *G06T 7/0014* (2013.01); *G06T 7/10* (2017.01); *G06T 15/205* (2013.01); *G06T 17/20* (2013.01); *A61B 5/0044* (2013.01); *A61B 5/1079* (2013.01); *A61B 5/319* (2021.01); *A61B 5/339* (2021.01); *A61B 2576/023* (2013.01); *G06T 2200/04* (2013.01); *G06T 2200/08* (2013.01); *G06T 2207/10024* (2013.01); *G06T 2207/10081* (2013.01); *G06T 2207/20081* (2013.01); *G06T 2207/30048* (2013.01); *G06T 2207/30061* (2013.01)

(58) Field of Classification Search
CPC ............ A61B 5/04028; A61B 5/04085; A61B 5/04286; A61B 5/0422; A61B 5/0077; A61B 5/7267; A61B 5/742; A61B 2562/04; A61B 2562/06; A61B 2562/063; A61B 2562/066; A61B 2562/046; A61B 2562/043; A61B 6/5247; A61B 6/022; A61B 6/461; A61B 6/503; A61B 6/5205; A61N 1/0412; A61N 1/0492; G16H 30/00; G06T 7/10; G06T 7/0012; G06T 7/0014; G06T 15/205; G06T 17/20; G06N 20/00

See application file for complete search history.

(56) References Cited

U.S. PATENT DOCUMENTS

| | | | |
|---|---|---|---|
| 9,569,736 | B1 | 2/2017 | Ghesu et al. |
| 2009/0208079 | A1* | 8/2009 | Vaillant .................... G06T 7/30 382/131 |
| 2012/0035459 | A1* | 2/2012 | Revishvili .............. A61B 5/318 600/411 |
| 2015/0038862 | A1* | 2/2015 | Gijsbers ................... A61B 5/25 600/509 |
| 2016/0007852 | A1* | 1/2016 | Warner ................ A61B 5/6858 600/374 |
| 2017/0071492 | A1* | 3/2017 | van Dam ............... A61B 6/037 |
| 2017/0103532 | A1 | 4/2017 | Ghesu et al. |
| 2017/0185740 | A1 | 6/2017 | Seegerer et al. |
| 2017/0249423 | A1 | 8/2017 | Wang et al. |
| 2017/0330075 | A1 | 11/2017 | Tuysuzoglu et al. |

OTHER PUBLICATIONS

Huang, T. M., Kecman, V., & Kopriva, I. (2006).Kernel based algorithms for mininghuge data sets: Supervised, semi-supervised, and unsupervised learning.Studies incomputational intelligence(vol. 17). Secaucus, NJ, USA: Springer.*

English Translation of CN 107203988 (Year: 2017).*

Zheng, Yefeng, et al. "Four-chamber heart modeling and automatic segmentation for 3-D cardiac CT volumes using marginal space learning and steerable features." IEEE transactions on medical imaging 27.11 (2008): 1-14.

International Search Report dated Apr. 4, 2019 in corresponding International Patent Application No. PCT/EP2018/085804.

Ghanem R. N. et al.: "Heart-surface reconstruction and ecg electrodes localization using fluoroscopy, epipolar geometry and stereovision: application to noninvasive imaging of cardiac electrical activity"; 2003; IEE Transactions on Medical Imaging; vol. 22; No. 10; pp. 1307-1318.

\* cited by examiner

NON-INVASIVE ELECTROPHYSIOLOGY MAPPING BASED ON AFFORDABLE ELECTROCARDIOGRAM HARDWARE AND IMAGING

TECHNICAL FIELD

The present teachings relate generally to electrophysiology (EP) mapping.

BACKGROUND

At the time of treatment (e.g. arrhythmia ablation) or for diagnosing complex cases, comprehensive assessment of the cardiac electrical signal is desired. 12-lead ECG is the method of choice for assessing and monitoring cardiac electrophysiology (EP) abnormalities in patients in general, but is still hard to read and interpret for non-experts. The precise localization of the disease focus from the ECG traces is also challenging. Invasive mapping systems provide high resolution spatio-temporal maps of cardiac potentials on the endocardium or epicardium, but are invasive and are expensive in terms of both time and money.

Other non-invasive systems use a vest of electrodes (e.g., 128 or 256 electrodes) that measure the body surface potentials everywhere. Coupled with a chest computed tomography (CT) scan, the epicardial potentials are reconstructed using back projection from the CT image of the heart and the vest provided electrode positions. However, these methods are limited as CT may not be available, the vest is an expensive one-time use device, and the setup adds extra steps in the already complicated clinical workflow. Methods that enable visualizing cardiac epicardial EP maps directly from a 12-lead ECG signals instead of the vest of electrodes still use preoperative three-dimensional (3D) imaging (MRI, CT), which is not part of the typical workflow and often not available. The standard ECG electrode positioning may also be sub-optimal for specific diseases or patients.

SUMMARY

By way of introduction, the preferred embodiments described below include methods, systems, and computer readable media with instructions for non-invasive EP mapping. A sparse number of electrodes (e.g., 10) are used to generate an EP map without requiring preoperative 3D imaging (but could still be used if available). An imager (e.g., a depth camera) captures the surface of the patient and may be used to localize electrodes in at position on the patient. Two-dimensional (2D) x-rays, which are commonly available, and the surface of the patient or the surface alone are used to infer the heart morphology of the patient. The EP map is then generated from the surface, heart segmentation, and measurements from the electrodes.

In a first aspect, a method is provided for EP mapping based on ECG hardware. A three-dimensional surface of a patient is detected from a sensor. A 3D model of a heart of the patient is formed from x-ray projection data and the three-dimensional surface. Electric potential is measured at ten or fewer locations on the patient with ECG electrodes. An EP map is generated for at least a part of the heart from the three-dimensional surface, the heart segmentation, and the measured electric potentials at the electrode locations. The EP map is displayed on a display screen.

In a second aspect, a system is provided for EP mapping. An image processor configured to estimate a surface of a patient from a red, green, blue, depth (RGBD) camera, estimate a heart mesh from the estimated surface and a heart shadow from one or more x-ray images output by an x-ray imager, and generate an EP map on the heart mesh from measurements of an ECG monitor based on the surface. A display is configured to display the EP map.

In a third aspect, a system is provided for EP mapping. An image processor is configured to estimate a three-dimensional surface of a patient from an imager, estimate a three-dimensional heart mesh for a heart of the patient from the estimated three-dimensional surface, and generate an EP map on the three-dimensional heart mesh from measurements of potential on a surface of the patient by electrodes of an ECG monitor, the EP map configured to be generated based on the surface. A display is configured to display the EP map.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

This document presents a low-Cost, non-invasive EP mapping based on existing 12-Lead ECG or other ECG hardware and imaging hardware. The low-cost system for non-invasive imaging of cardiac EP is based on ECG measurements and x-ray imaging systems already available in a standard cathlab. Other medical imaging systems may be used if available, but are not required. Not all the 10 electrodes are necessary, so two electrodes may be used.

In one embodiment, epicardial, endocardial or myocardial EP maps (e.g., local activation time, potentials, deactivation, conduction velocity, and/or others) are generated. A 3D avatar of the patient is estimated using an optical or RGBD camera, or any another imager. The 3D avatar is a digital representation of patient's body, including at least the thorax. ECG electrodes on the patient are localized on the 3D avatar using the RGBD camera or imager. The ECG electrodes may be placed anywhere on the patient torso, such as placements guided by the system or based on other criteria, rather than standardized locations. A 3D heart model is estimated from the heart shadow seen in 2D x-ray images and the 3D avatar. More x-ray views may be used to increase the accuracy of the model. Optionally, a 3D lung model is estimated from the x-ray image or images and the 3D avatar. Myocardial or other EP map is estimated from the 3D avatar, heart model, optionally the lung model, and measurements from the ECG electrodes. The computed EP map or maps are displayed on a screen.

Figure 1:
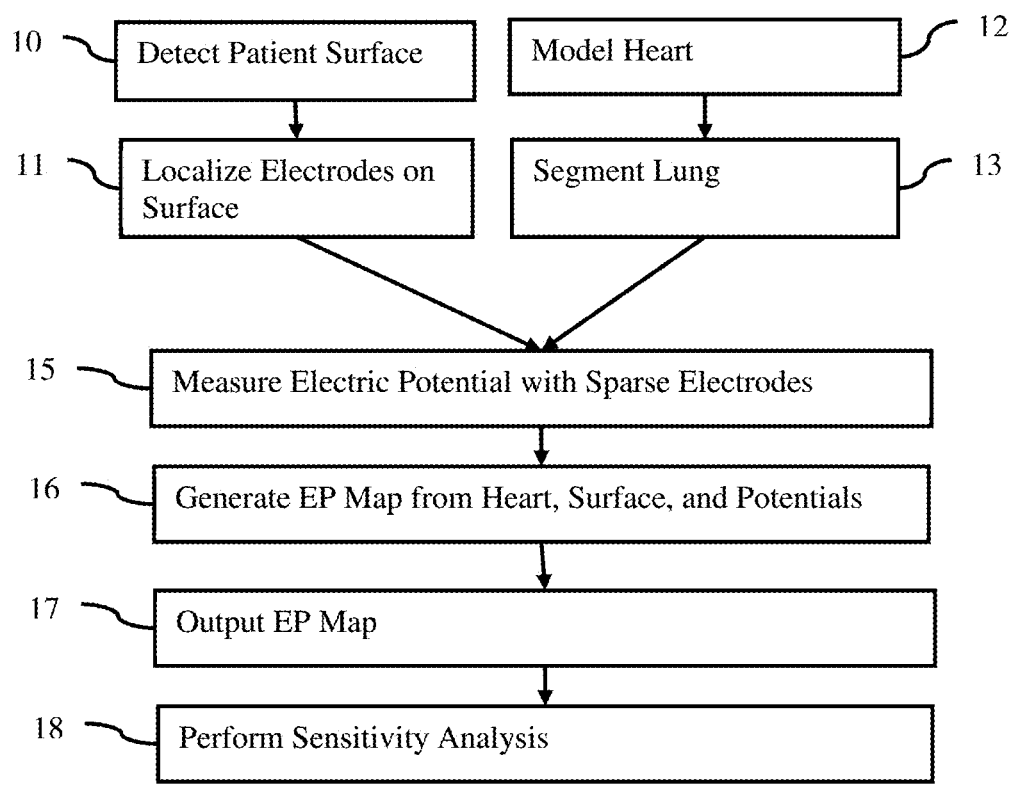
FIG. 1 is a flow chart diagram of one embodiment of a method for EP mapping based on ECG and imaging hardware.

FIG. 1 shows one embodiment of a method for EP mapping based on ECG hardware. The method includes sparsely measuring potential on an exterior surface of the patient, determining a heart surface for that patient, detecting the exterior surface, and generating the EP map on the heart surface based on the sparse measurements and the detected exterior surface.

The method of FIG. 1 may include additional, different, or fewer acts. For example, act 13 is optional. As another example, act 18 is optional or not performed. In yet another example, acts 15 and 16, with or without acts 10, 11, 12, and/or 13, are repeated to output the EP map in act 17 based on new electrode positions determined in act 18.

The acts are performed in the order shown (top to bottom or numerical) or a different order. For example, acts 10 and 11 are performed before, after, or simultaneously with acts 12 and 13. Act 18 may be performed prior to act 15, such as due to repetition.

A medical scanner, processor, server, workstation, computer, other device, or combinations of devices perform the acts of FIG. 1. In one embodiment, the system of FIG. 7 performs the method. In other embodiments, a medical imager, image processor, or remote server performs the acts based on measurements from an ECG monitor, photographs or video from a camera, and one or more images from an x-ray scanner.

In act 10, an image processor detects a 3D surface of a patient from a sensor. The 3D surface is an exterior surface of the patient with or without clothes or a covering sheet. The 3D surface is used in determining a spatial distribution of electrical potential including the measured potentials from the ECG monitor and for segmenting the heart and/or lungs.

The sensor is a optical or depth camera. One or more red, green, blue, depth channels (RGBD) or other types of cameras are used. A still image, video, with or without depth information is used to compute the 3D surface of the patient as positioned for ECG measurement, EP mapping, and/or x-ray imaging. The camera image is used to create a point cloud, surface mesh, or other three-dimensional representation of the patient. Alternatively, stereo cameras without depth measurements are used.

For the depth camera, a depth sensor measures depths relative to a surface of a patient. Any depth sensor may be used. The depth sensor provides 3D sensor image data or depth data. Any now known or later developed depth camera may be used, such as stereo cameras, structured-light devices (e.g., Microsoft Kinect, ASUS Xtion), time-of-flight devices (e.g., Creative TOF cameras), and combinations thereof. In some embodiments, the 3D sensor image data further includes color image data (e.g., an RGB image). Any optical depth camera may be used to measure the surface of the patient, with or without clothes. In one embodiment, the depth measurements from the sensor provide a 3D point cloud of the patient. The 3D point cloud may be reconstructed and used for further processing. Data may also be captured from multiple cameras and fused to obtain a more accurate 3D point cloud.

The placement of one or more cameras in the medical image scanning room (e.g., cathlab, x-ray imaging room, and/or the like) may be determined empirically to achieve optimal performance of the analytics. Various factors that may influence performance include, for example, the ease and/or expense of sensor installation, patient visibility constraints (e.g., the quality of the obtainable data), and sensor noise characteristics. For example, with structured-light devices and time-of-flight devices, noise tends to increase as distance from the sensor increases. Moreover, depending on wavelength, noise may also increase near the sensor. Thus, sensor noise characteristics may be balanced against the field of view of the sensor when determining placement of a sensor.

To achieve reliable surface reconstruction from depth images, the cameras may be mounted such that the cameras have an unobstructed view of the patient lying or positioned on the patient table. Depending on the sensor noise characteristics (e.g., image quality and/or resolution of captured depth-image), the camera(s) may be mounted close to the scanner table while still being able to keep the entire or majority of the patient within the camera view.

Only one or more than one camera may be used, such as a first camera positioned on the ceiling directly above a patient table, and a second camera positioned at one end of the patient table. The two locations—overhead and angled—each have their advantages and disadvantages. In one embodiment, the camera is positioned on a housing of an x-ray source that may be positioned relative to the patient (e.g., positioned by a robotic arm).

Figure 2:
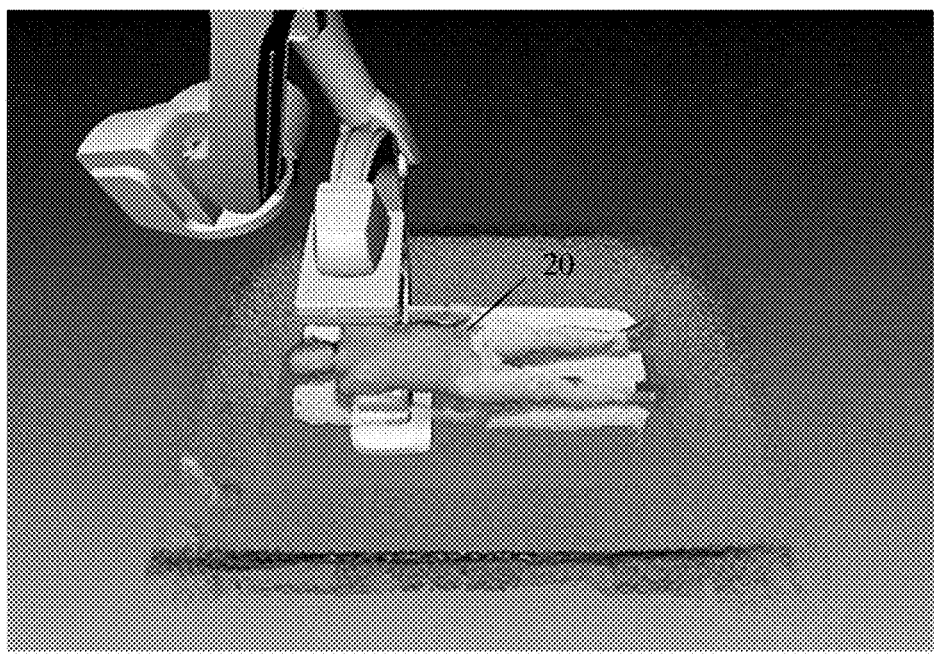
FIG. 2 illustrates an example three-dimensional (3D) surface of a patient from a RGBD camera.

The depth information is processed to identify the surface. For example, a 3D surface with curvature constraints is fit to the depths or point cloud. In another example, an average, prior, or template surface of a person is fit to the depths or point cloud from the sensor. A human model may be fit, based on application of a machine-learnt network or other optimization, to the depths or point cloud. The pose, body parts, and/or other parameterization of the exterior surface of the patient is estimated as the 3D surface of the patient. The 3D surface may be parameterized in any manner, such as a 3D mesh. FIG. 2 shows an example rendering of a 3D surface 20 detected by a camera. The 3D surface is an avatar fit to the patient using a RGBD camera.

In alternative embodiments, the 3D surface is a mean model fit to or selected based on a height and weight of the patient. In another alternative, a computed tomography (CT), magnetic resonance (MR), ultrasound (US), or other 3D medical scanner scans the patient, and the 3D surface is segmented from the scan data.

In act 11, the image processor localizes ECG electrodes on the 3D surface. The patient has any number of electrodes, such as 10 or fewer, 20 or fewer, or 64 or fewer, placed on their skin. There are fewer electrodes used than in a typical vest system (e.g., fewer than 128 or 256). The surface is detected in act 10 while the electrodes are positioned on the patient. The position of the electrodes on the surface or avatar of the patient is then determined.

The localization of the electrodes on the patient chest is straightforward. Since the patient is mapped in real-time, directly from the interventional bed, no co-registration is necessary, and the electrodes may be positioned on the 3D avatar model directly. The same sensor or imager used to detect the patient surface is used to localize the electrodes.

In one embodiment, the image processor localizes the electrodes with a depth camera used for the detecting the 3D surface and a machine-learnt network. To detect the electrodes in the RGBD images, a machine learning approach is employed. The machine-learnt network is trained on a large number of video streams, photographs, and/or fit 3D surfaces annotated to indicate the locations of electrodes. The machine learns to detect the location of electrodes based on these many samples and the ground truth electrode locations for the samples. Any type of machine learning and resulting machine-learnt network may be used, such as image-to-image deep networks (e.g., convolutional-deconvolutional deep neural network), deep reinforcement learning, support vector machine, other neural network, recurrent network, or Bayesian network. For machine learning other than deep learning, any input feature vector may be used, such as Haar wavelets. Other approaches (e.g., not machine-learnt networks) may be used, such as pattern matching with correlation. Manual indication of the electrode positioned from a user on an image of the exterior of the patient or rendering of the 3D surface may be used.

In interventional setup, the patient may be covered with a sheet for hygiene and sterility purposes. The sheet may hide some electrodes and parts of the patient's chest. To cope with this situation, the 3D avatar model and electrode positioning of acts 10 and 11 are performed before the intervention starts. The patient is first positioned on the bed. Electrodes are placed on the patient. The 3D avatar model is estimated in act 10, along with the electrode position being determined in act 11. The patient is then prepared for the intervention. To track potential patient motion, a second avatar, with a sheet, may be estimated and used as reference to automatically update the patient pose.

Figure 3:
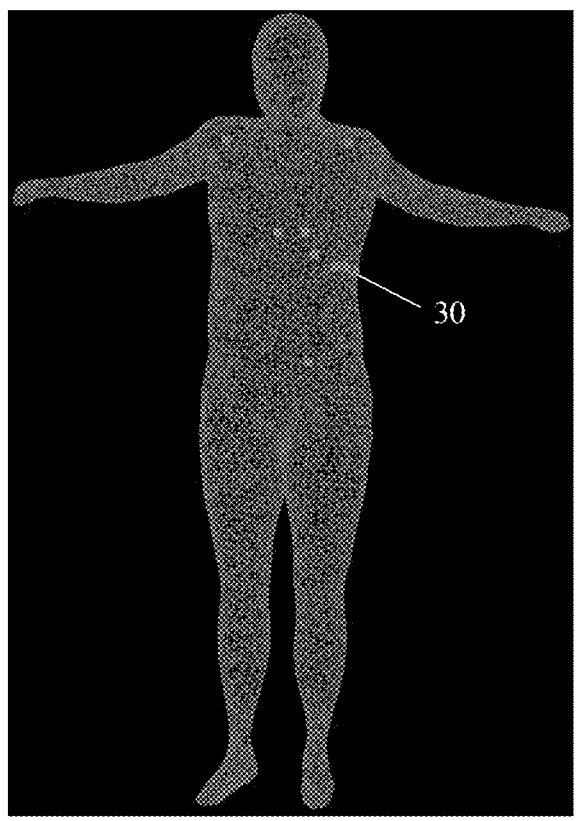
FIG. 3 illustrates an example electrode localization on a 3D surface of the patient.

FIG. 3 shows an example of a 3D avatar or surface of the patient represented as a mesh with the locations of electrodes 30 shown as larger dots. In this example, the 10 electrodes used in 12-lead ECG are generally positioned at standard locations, but non-standard locations may be used. At least one of the ECG electrodes may be placed on the patient at a non-standard location relative to 12-lead or 3-lead ECG. Due to localization of the electrodes, standard electrode positioning is not assumed. The electrodes may be placed anywhere for optimal EP mapping. Any number of electrodes may be used, such as just electrodes for a 3-lead ECG monitor or higher numbers of electrodes (e.g., 3-10 or more). Cost may be saved by using already available 3 or 12-lead ECG monitoring.

Electrodes may be positioned on the back of the patient. In this case, acts 10 and 11 are repeated, once with the patient in the prone position and once with the patient in the supine position.

In alternative embodiments, the electrodes are localized by assuming standard positions or by assuming proper placement based on guided or instructed placement. For example, a projector mounted with the RGBD camera projects light dots to indicate where the electrodes are to be placed. In another alternative embodiment, the locations are localized from an x-ray image. Fluoroscopy imaging may show electrode placement. A machine-learnt detector or other segmentation is applied to the x-ray image to detect the locations of the electrodes. Multiple approaches may be used, and the results combined or averaged.

In act 12, the image processor models the heart of the patient. The heart is segmented for the patient. The segmentation provides a 3D surface, such as a mesh. The heart surface is a base or spatial representation on which the EP map is to be created.

In one embodiment, the heart is modeled from 3D imaging data. For example, a preoperative or intraoperative scan is performed. MR, CT, 3D US, or other 3D scan provides data represented tissue of the patient in three dimensions. Any segmentation may be applied, such as based on intensity thresholding or machine-learnt classification. The segmentation locates one or more surfaces of the heart, such as a heart boundary, myocardial wall, or endocardial wall. The 3D surface of the patient is spatially registered with the heart segmentation or scan data. For example, the RGBD camera is at a known and calibrated position relative to the medical imager. The registration spatially aligns the 3D exterior surface with the interior heart surface.

Since a 3D scanner may not be available, the heart modeling may use x-ray projection data and the 3D surface. The heart is modeled in three dimensions from 2D x-ray projection data. A single x-ray or multiple x-ray images from different directions relative to the patient may be used. Alternatively, the heart is modeled from the 3D surface without other medical imaging. A heart prior or standard shape may be altered based on the 3D surface in order to model the patient.

The x-ray image or images are used to form a heart mask. The projection data represents the heart in two dimensions. The heart mask indicates locations where the heart is located in those two dimensions. Any segmentation or detection may be used to form the heart mask. In one embodiment, a deep machine-learnt neural network is applied. The x-ray image is input to the neural network, which outputs the heart mask or heart locations. The neural network is trained with deep learning to segment the heart from x-ray images. In one embodiment, a deep convolutional-deconvolutional network (e.g., image-to-image network) architecture is used. Other architectures, such as a dense net, U-net, or generative model, may be used. Any machine-learnt segmentation or non-machine-learnt segmentation may be used.

Figures 4A, 4B:
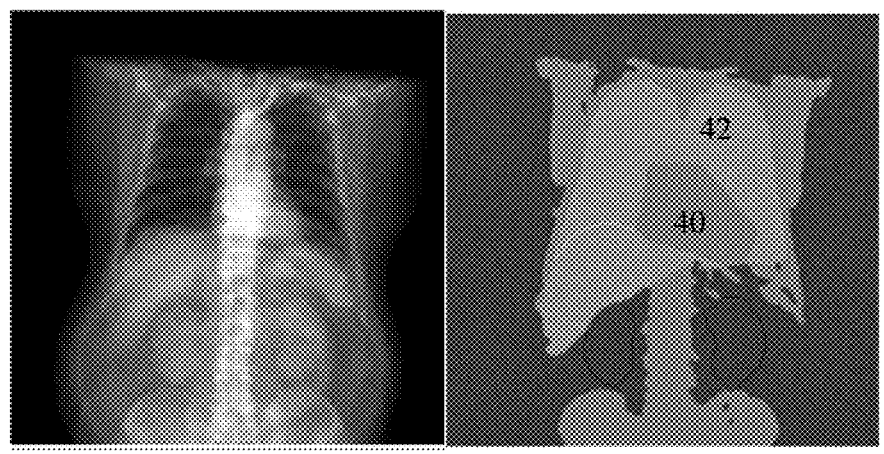
FIG. 4A is an example x-ray image of a torso of a patient.
FIG. 4B is an example mask segmentation for the heart and lungs in the x-ray image of FIG. 4A.

FIGS. 4A and 4B show an example. FIG. 4A is an x-ray image of x-ray projection data through a torso of a patient. The x-ray image or projection data is input to the deep machine-learnt neural network, which outputs a binary mask 40 of FIG. 4B representing the locations of the heart. The binary mask 40 provides a heart shadow or projection of the heart to the imaging or x-ray detector plane.

The heart mask 40 is 2D. For EP mapping, a 3D representation may be desired. A 3D heart mesh or other 3D heart surface representation is formed for the heart from the 2D heart mask 40 and the 3D exterior surface of the patient. Any extrapolation of the 2D heart mask 40 to the 3D heart using the 3D surface may be used. In one embodiment, a machine-learnt regression model is applied. The 2D heart mask and 3D surface are input to the regression model, which outputs the 3D heart surface. Other inputs may be used, such as x-ray data or shape prior. The regression is a learnt function relating the input to the output. The 3D model of the heart is regressed from the heart shadow or shadows and the 3D avatar.

The regression model is machine trained. A large set of CT cardiac scans are gathered. The heart is segmented using automated or manual methods from the CT scans. These segmentations provide a ground truth. Hyper-realistic digitally reconstructed radiographs (DRRs) are generated from the CT scans using projection and generative deep learnt models to create 2D x-ray images from different view directions. A 2D mask per x-ray view of the 3D heart model is also projected to form the ground truth. The regression is then learned, given the 3D avatar, the x-ray image, and the heart segmentation, to provide the 3D heart mesh directly from the 3D surface and the heart shadow.

To facilitate the learning task, the different 3D heart shapes may be projected onto a common shape space parameterized with a few parameters, such as using principle component analysis (PCA). Since the 3D segmentation provides point correspondence across patients, a point-distribution model may straightforwardly be calculated. The output of this step is a reconstructed 3D heart shape, regressed from the x-ray images, heart mask 40, and the 3D avatar. Other embodiments may consider only the x-ray images (no avatar), rely on DynaCT images, preoperative images, or a combination of the above.

In act 13 of FIG. 1, the image processor segments or models the lungs of the patient. The segmentation is from any scan data. In one embodiment, the segmentation is from the x-ray projection data used for segmenting the heart. The lung segmentation may be performed in the same or different way discussed above for heart segmentation. For example, one machine-learnt network is used to form a lung mask (see mask 42 of FIG. 4B) from an x-ray image or projection data. Another machine-learnt network finds the 3D distribution or boundaries of the lungs from the lung mask and the 3D surface.

The x-ray images may need to be zoomed out or cover the lungs rather than only part of the lungs, such as is provided with chest x-ray scans. Different types of x-ray may be used to segment the lung and the heart if needed (e.g. angiography for the heart, and standard x-ray for the lung).

The heart, optionally the lung, 3D surface, and electrode localization acts are performed once to be used for EP mapping over time. Alternatively, acts 10-13 are repeated for different times to account for patient or other motion. A sequence of 3D heart surfaces, 3D exterior surfaces, electrode positions, and optionally lung locations are estimated. Alternatively, the acts are performed initially, and the surfaces or locations are tracked over time using other processes, such as correlation.

Figure 6:
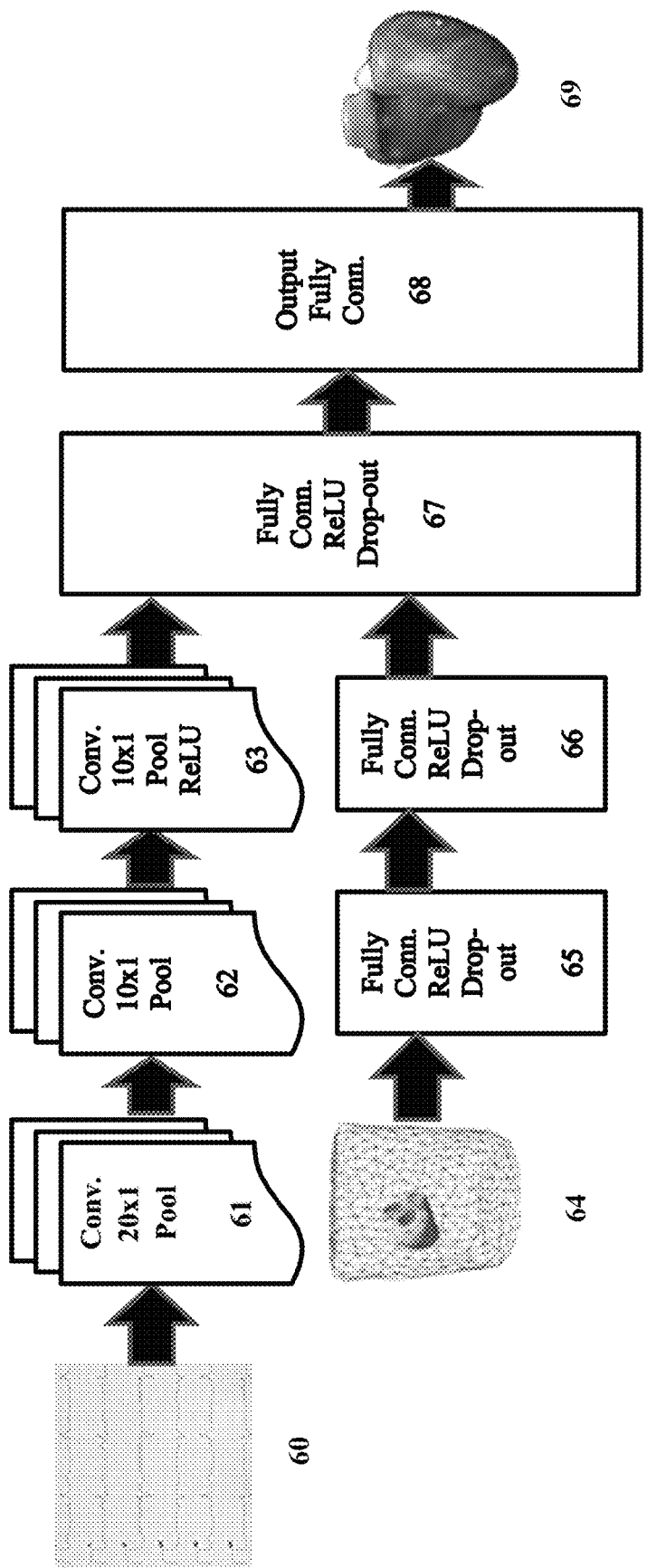
FIG. 6 is one embodiment of a neural network architecture for virtual heart model-based EP map generation.

In act 15, an ECG monitor measures electric potential. Each of the electrodes is used to measure potential at the skin of the patient. The potential is measured at one time or measured over time. For example, FIG. 6 shows six traces 60 representing potential measured at six electrodes over time. The potential may be an absolute measure or may be a difference between two electrodes. Other potential information may be derived from the electrode signals.

The potential is measured sparsely. For example, the potential is measured at ten or fewer (e.g., 2 or 3) locations. More locations may be used. Rather than requiring a vest with 128 or 256 electrodes, fewer electrodes by at least half are used. Due to the sparse measurement, many nodes or locations on the 3D surface of the patient are not associated with measurements. Some locations are associated with measurements.

In act 16, the image processor generates an EP map. Any EP map may be generated, such as electric potential, local activation time, deactivation time, or convection velocity. The EP map may represent EP operation of the heart at a given time or over time. A sequence of EP maps representing EP operation of the heart at different times may be generated. Any part of the heart may be included or used for the EP map, such as the myocardium or epicardium.

The EP map is spatially represented by a heart surface. The potential measurements are sparse and at the exterior surface of the patient. The image processor determines the EP operation on the surface of the heart from the sparse measurements on the exterior of the patient. The EP map is generated for at least a part of the heart from the 3D surface, the heart segmentation, and the measured electric potentials at the sparse locations. Once the anatomical model (e.g., torso (3D surface)+heart segmentation+optionally lungs) is estimated, the EP myocardial map is estimated.

In one embodiment, the heart potentials are inverse mapped from the measured electric potentials from the electrodes. A transfer matrix relates the potentials at the 3D surface to the potentials at the heart. Direct inverse mapping is applied. Knowing the transfer matrix T from the heart to the torso, calculated using boundary element methods, the objective is to find the cardiac potentials U such that $\|TU|_\Omega - B|_\Omega\|$ is minimized, with B the measured body surface potentials, and $\Omega$ the measurement domain (e.g., 10 points in the case of 12-lead ECG). This optimization problem is known to be highly ill-posed, even in the case where $\Omega$ is the full torso (e.g., 128 or 256 electrodes). Various regularization techniques may be employed, such as $L_p$ norm coupled with $L_q$ regularization (0<p, q<=2), temporal smoothing, and action potential shape matching.

Where the lungs are segmented, the transfer matrix may account for the lung tissue in the inverse mapping. The electrical characteristics of the lungs or air in the lungs is different than other tissue. Using the locations of the lungs and the electrical characteristics of the lungs, the transfer matrix may more accurately inverse map the potentials from the surface to the heart through the lungs.

For further increase in accuracy of the inverse mapping, the image processor reconstructs a body surface potential map from the measured electric potentials. The sparse measurements are extrapolated to other locations on the 3D surface, reducing sparsity. The reconstructed body surface potential map has a greater density of potentials than the measured electric potentials.

Any reconstruction may be used. In one embodiment, a machine-learnt mapping from the localized positions of the ECG electrodes and the 3D surface are used to reconstruct the body surface potential map. Given the sparse body surface measurement locations (e.g., 10 or fewer locations), a denser body surface potential map is reconstructed using machine learning techniques. For example, potential signals for the full body surface (e.g., each node of the mesh) are formed from the sparse measurements. In one approach, dictionary learning, where the dictionary entries are learned from a large database of densely measured body surface mapping, is used. The resulting machine-learnt dictionary is used to generate the body surface potential map from the sparse measurements, electrode locations, and the 3D surface as inputs. In another approach, a generative adversarial network (GAN) is trained, where the input is the measured points or locations, the measurements, and the 3D surface. The output is the reconstructed field on the entire torso or 3D surface. The GAN is trained on a large database of dense body surface maps, from which ECG signals are extracted, for other people. The database may be augmented or formed using simulated potentials from a virtual heart model that includes electrophysical modeling.

Figure 5:
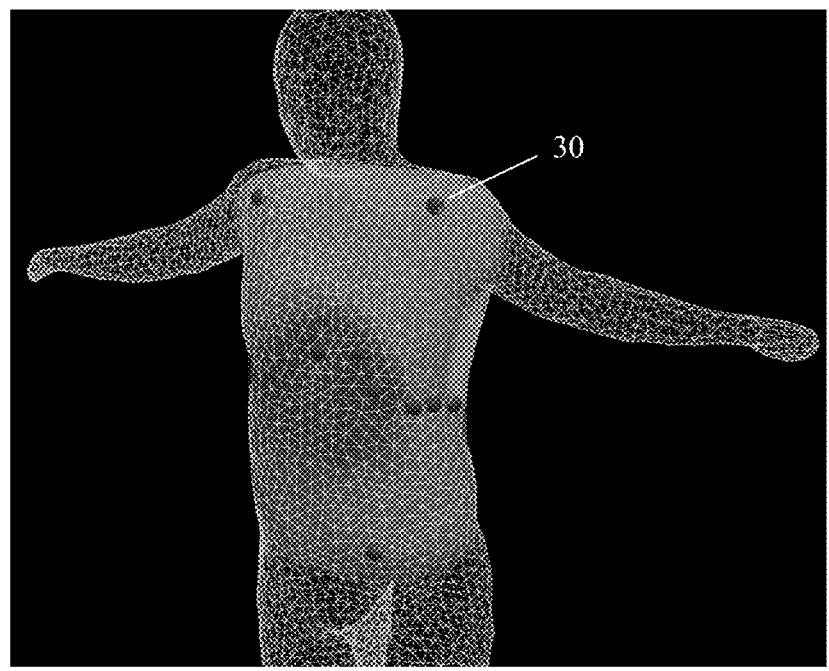
FIG. 5 is an example surface map of potential extrapolated from measured potentials.

FIG. 5 shows an example reconstructed torso potential map. The potentials at the electrodes 30 are known from measurements. The mesh is provided by or as the 3D exterior surface of the patient. For the torso part of the mesh, the intensity of the gray-scale represents the potential. The potentials for different nodes or locations on the 3D surface are estimated by the machine-learnt network.

Once the denser body surface map of potentials is estimated, the image processor back projects the potentials to the heart surface, such as using the transfer matrix. In another embodiment, a machine-learnt image-to-image network (e.g., a deep trained convolutional-deconvolutional neural network) outputs the EP map or back propagation. The image-to-image network is trained to directly learn the mapping from the denser body surface potential map to an EP map. Back propagating from the denser potential map may increase the accuracy of the generated EP map.

In an alternative embodiment for generating the EP map, a heart model including EP modeling is used to generate the EP map. The image processor solves for tissue properties of the heart and/or other parameters of the heart model and determines the EP map from the virtual heart model with the tissue properties and/or other parameters. The measured potentials are used to estimate the tissue properties. For example, deep learning trains a neural network to estimate tissue conductivities from the traces of the 12-lead electrocardiogram. Other tissue properties may alternatively or additionally be included in the modeling, such as actuation time or reaction potential duration. The tissue properties are for the heart, lungs, skin, and/or other tissue. Once the tissue properties are estimated, the virtual heart model estimates the EP map (e.g., potentials) based on the tissue properties. Since the virtual heart model is personalized to the patient by the tissue properties, the EP map for that patient is determined. The EP map or the virtual heart model may be fit to the segmented heart of the patient. The 3D surface and localization of the electrodes are used in the solution of the tissue properties. Since the virtual heart model is available, the potentials anywhere in the heart, including mid-myocardium and endocardium, are available.

FIG. 6 shows one example architecture of the virtual heart model as a neural network outputting an EP map 69. The ECG measurements 60 are input to solve for tissue properties to convolutional and pooling layers 61, which output to other convolutional and pooling layers 62, which output to convolutional and pooling layers 63 including a rectified linear unit (ReLU). The 3D surface and heart segmentation 64 are input to a fully connected ReLU drop out layer 65, which outputs to another fully connected ReLU drop out layer 66. The output from these two paths are input to a fully connected ReLU drop out layer 67, which outputs to a fully connected layer 68. Other architectures, layers, and/or networks may be used. This virtual model is trained to output the EP map given the inputs 60, 64. The network infers the tissue properties and the cardiac EP maps directly from the input 3D surface, ECG measurements, electrode locations, and heart segmentation.

In act 17 of FIG. 1, a display device displays the EP map. The image processer generates an image of the EP map and causes the image to be displayed on the display screen.

Any EP map image may be displayed. Change over time in the potential at the heart may be used to derive the EP map image, such as local activation or deactivation time map. The potentials at a given time may be used. A dynamic potential propagation movie of potential maps over time may be used. Any EP map may be used.

The image includes the EP map alone. Alternatively, the EP map is displayed with other information, such as the x-ray image and/or ECG traces.

The EP map covers a 3D heart surface, so the image is created by rendering the EP map to a 2D image. Direct volume rendering, surface rendering, or other type of rendering of the heart mesh may be used. The EP map or potential information modulates the color, brightness, and/or intensity of the voxels or pixels. In other embodiments, the EP map is rendered as a bull's-eye view of the heart. Other types of EP map imaging may be used.

Due to the use of easily available x-ray imaging and the camera, an ECG monitor may be used to provide EP maps with greater accuracy or spatial resolution than using an ECG alone. A 3D medical scanner is not needed, allowing lower cost use and use at medical facilities with no or limited access to 3D medical scanners.

In act 18, the image processor performs a sensitivity analysis using the EP map and outputs a change in position for at least one of the ECG electrodes. The change is a new position or a difference in position. The best or better positions for electrodes are determined for optimal EP mapping specific to that patient. One or more EP maps are generated using electrodes positioned in a standard fashion (e.g. just two electrodes or standard 10 electrode positioning). Previously determined, other generalized, or random positioning may be used. First estimates of the EP maps are obtained, along with a virtual heart model. The tissue properties and other parameters for the virtual heart model are determined.

An automated sensitivity analysis is performed to optimize the position of the electrodes on the patient for maximal EP mapping accuracy. The virtual heart model allows simulated placement of the electrodes at different locations. Using a standard or expected ECG trace, the sensitivity of the EP maps to different electrode positions is modeled. The positions having the greatest impact on the EP map or maps are determined. The resulting electrode positions are then displayed to the user or directly projected to the patient. The actual electrodes are then repositioned to these optimal locations for that patient, and the method (e.g., acts 10-17) for generating EP maps is repeated to create the EP map to be used for diagnosis.

The virtual heart model may be used to assess the areas of uncertain measurements. The EP map estimated from the heart model is compared with the EP map generated by back propagation. The locations of largest difference indicate heart tissue with uncertainty for the related measurements. These areas may then be investigated using more invasive EP mapping systems. For example, an intra-cardiac ECG measurement is performed at the areas of uncertainty to improve the estimation.

If invasive intracardiac ECG measurements are available, the invasive measurements may be incorporated. Using variational data assimilation or other optimization, the EP map is refined to better fit with the invasive intracardiac measurements. The intracardiac measurements may be sparser due to the EP map generation from the ECG monitor than without. Any density of intracardiac measurement may be used.

In other embodiments, the ECG signals and images are augmented with other surrogate signals for improved accuracy. The image with the EP map may be annotated to include other information, such as pressure or impedance. The EP maps may be shown in sequence correlated with heart sound. Magnetic cardiac recordings may be displayed with an EP map. The same or other information may be used in any of the acts. For example, impedance is measured for the patient. The impedance is used to limit and/or influence the heart segmentation. Heart sound measures may be used for timing, such as a motion prior for the EP map.

Figure 7:
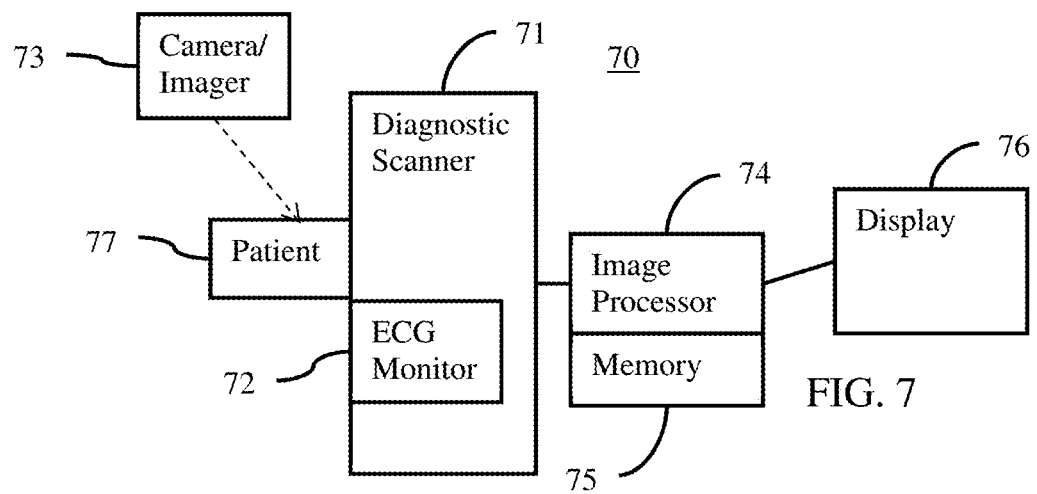
FIG. 7 is a block diagram of another embodiment of a system for EP mapping.

FIG. 7 shows one embodiment of a system 70 for EP mapping. The system implements the method of FIG. 1 or a different method. By imaging the exterior surface of the patient, sparse ECG measurements (e.g., 10 or fewer) may be used with a 2D medical scanner 71 to create EP maps. Rather than relying on 3D medical scans or dense ECG measurements, a simple imager 73 and commonly available medical scanner 71 are used.

The system 70 is at a point of care for a patient 77, such as in a room, hospital, catheter laboratory (cathlab), or imaging center. The image processor 74, memory 75, and display 76 may be part of the diagnostic scanner 71 in one embodiment, such as being an x-ray workstation. In other embodiments, the image processor 74, memory 75, and/or display 76 are part of a separate computer, such as a separate workstation, personal computer, laptop, or tablet. In other embodiments, the image processor 74, memory 75, and/or display 76 are at other locations, such as a different building.

The image processor 74 and/or memory 75 may be part of a server. In other embodiments, the memory 75 is a database separate from the image processor 74.

The system 70 includes the imager 73, the diagnostic scanner 71, the ECG monitor 72, the image processor 74, the memory 75, and the display 76. Additional, different, or fewer components may be provided. For example, a speaker is provided for playing heart sounds. As another example, a user input device is provided for the user to configure or activate the diagnostic scanner 71, the imager 73, and/or EP map generation. In yet another example, the imager 73 is not provided, such as where scan data is used instead of a depth image.

The diagnostic scanner 71 is a medical diagnostic imaging device or scanner. For example, the diagnostic scanner 71 is an x-ray scanner or imager, such as for generating 2D projection data. 2D images may be generated from different directions relative to the patient 77, but without reconstruction to a 3D representation of the patient. A C-arm system may be used. Fluoroscopy, angiography, or other cardiac x-ray systems may be used. In alternative embodiments, the diagnostic scanner 71 is CT scanner with an x-ray source and detector connected on a gantry that moves relative to a patient bed. The CT scanner may be used to generate 2D projections and/or reconstruct a 3D representation. In alternative embodiments, an MR, PET, SPECT, ultrasound, or other medical imaging system is used.

The ECG monitor 72 includes electronics for measuring potential or differences in potential from leads. The ECG monitor 72 may have inputs or ports for leads. The leads connect electrodes 30 to the ECG monitor 72. The ECG monitor 72 includes a display for displaying ECG traces, derived heartbeat, or other information. Alternatively, the display 76 of the system is used.

The ECG monitor 72 is a stand-alone device with an output connectable to the scanner 71 and/or the image processor 74. Alternatively, the ECG monitor 72 is built into or part of the diagnostic scanner 71.

The imager 73 is any imager for sensing an exterior of the patient. The imager 73 may be a medical scanner, such as a CT, MRI, or ultrasound for scanning in 3D. In one embodiment, the imager 73 is a depth camera, such as a red green blue depth (RGBD) camera or camera with a depth sensor. Stereo cameras, structured light transmission with a camera as the sensor, time-of-flight sensor with a transmitter, or other now known or later developed sensor for determining depth is provided as the imager 73. In one embodiment, the imager 73 is an optical RGB-D camera.

The imager 73 is configured to detect a surface of a body or object. The surface is detected in three dimensions. The imager 73 captures an image or images from which depth may be derived. Alternatively, the imager 73 directly captures a 3D point cloud of different depth measurements. Image processing may be applied to remove background. Alternatively, the background remains and is dealt with as part of mesh fitting to estimate the 3D surface of the patient 77.

The patient 77 is positioned relative to the imager 73, such as on the bed of the diagnostic scanner 71. Where multiple imagers 73 are provided, the imagers 73 are directed to view the patient 77 from different directions. Depth data representing the surface of the patient is acquired from the different imagers 73 and used together to create a unified point cloud or surface representation.

The surface of the patient 77 is the skin of the patient 77. Alternatively, the surface of the patient 77 is clothing of the patient 77 or a sheet over the patient 77. The surface may be low pass filtered to remove high frequency variation. Depth information for combinations of skin and clothing may be detected.

The image processor 74 is a general processor, central processing unit, controller, control processor, graphics processor, digital signal processor, three-dimensional rendering processor, image processor, application specific integrated circuit, field programmable gate array, digital circuit, analog circuit, combinations thereof, or other now known or later developed device for generating an EP map based on data from the imager 73, ECG monitor 72, and the scanner 71. The image processor 74 is a single device or multiple devices operating in serial, parallel, or separately. The image processor 74 may be a processor of a computer, such as a laptop or desktop computer, or may be a processor for handling some tasks in a larger system, such as in a medical imaging system (e.g., diagnostic scanner 71). The image processor 74 is configured by instructions, design, hardware, and/or software to perform the acts discussed herein.

The image processor 74 is configured to estimate a surface of the patient 77 from the imager 73, such as an RGBD camera. Based on a point cloud, depth measurements, fitting of a model or template, and/or segmentation of the exterior surface of the patient, a 3D mesh representing the exterior surface of the patient 77 is generated with image processing.

The image processor 74 is configured to estimate a heart mesh of the heart of the patient 77. The heart mesh is estimated from the estimated surface and a heart shadow from one or more x-ray images output by the x-ray imager (e.g., scanner 71). The heart mesh is a 3D mesh representation of the heart of the patient 77. A combination of one or more 2D images and the 3D exterior surface are used to find the 3D heart mesh. The 2D images may be used to find the heart shadow or projection specific to the patient. Any segmentation of the 2D x-ray image may be used, such as applying a machine-learnt neural network to generate the heart shadow. To extrapolate the 3D heart mesh from the heart shadow and 3D exterior surface, the image processor is configured to estimate the heart mesh by applying a machine-learnt regressor to estimate the heart mesh.

The image processor 74 is configured to generate an EP map. The EP map covers or is spatially distributed on the heart mesh. The EP map is derived from measurements of the ECG monitor 72 from the electrodes on the patient 77. Since those measurements are on the surface of the patient 77, the potentials at the heart are determined. The positions of electrodes on the 3D map are detected from output of the imager 73, such as by application of segmentation or a machine-learnt network.

Given the electrode localization and the 3D exterior surface, the ECG measurements are back propagated with a transfer matrix to the heart mesh. Alternatively, a machine-learnt network is used to generate the EP map on the heart mesh given the 3D surface, electrode localization, and heart mesh. In yet other embodiments, values for parameters (e.g., electrophysical characteristics of tissue) for a heart model are determined from the ECG measurements, 3D surface, heart mesh, and/or other information (e.g., pressure). The heart model is then used to model the EP map given the electrode localization, ECG measurements, heart mesh, and/or 3D surface.

In one embodiment, the image processor 74 is configured to generate the EP map from a reconstruction of a body surface potential map extrapolated from the measurements of the ECG monitor. The ECG measurements are extrapolated to other locations on the 3D surface. The extrapolation uses a machine-learnt network, which uses the ECG measurements, 3D surface, and electrode localization to output the potential map. Once the potential map on the 3D exterior surface is reconstructed, the potential map is back projected to the heart mesh or used as an input to a machine-learnt network for generating the EP map.

The image processor 74 generates an image from the EP map. For example, a rendering from a given viewing direction or a bull's-eye view image are generated. Any EP map visualization may be used.

The image processor 74 may output other information. For example, a sensitivity analysis is performed using a virtual heart model personalized to the patient 77. The locations to which electrodes should be moved are output. The image processor 74 may indicate locations of uncertainty or guide intracardiac measurements.

The memory 75 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 75 is part of the diagnostic scanner 71, part of a computer associated with the image processor 74, part of a database, part of another system, a picture archival memory, or a standalone device.

The memory 75 stores data used by the image processor 74. For example, the memory 75 stores output from the imager 73, the scanner 71, and/or the ECG monitor 72. In another example, the memory 75 stores a model, machine-learnt networks, and/or other data used to generate an EP map. As another example, the memory 75 stores data used in processing, such as a 3D surface (e.g., mesh), heart surface (e.g., mesh), and/or electrode positions on the 3D surface. In yet another example, the memory 75 stores results, such as an EP map or recommended electrode positions. Any data used, input to, output by, or created for the acts discussed herein may be stored in the memory 75 or another memory.

The memory 75 or other memory is alternatively or additionally a computer readable storage medium storing data representing instructions executable by the programmed image processor 74 and/or diagnostic scanner 71. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 76 is a liquid crystal display (LCD), an organic light emitting diode (OLED), a flat panel display, a solid-state display, a cathode ray tube (CRT), a projector, a printer, or other now known or later developed display device for outputting an image. The display 76 may be part of a user interface. The display 76 is configured by a display plane buffer or data provided by the image processor 74.

The display 76 is configured to display an EP map on the display screen. A rendering or other representation of the EP map as distributed on the heart mesh is displayed.

Various machine training and resulting machine-learnt networks are mentioned above. Other types of machine training and resulting networks may be used for any of the networks. For example, the machine-learnt model is implemented as a neural network. Such networks have a pool of shared layers to determine common features to the task at hand and additional layers that are trained for classification from the features. Any type of machine learning algorithm may be used, such as a support vector machine. The machine learning is supervised, semi-supervised, or unsupervised. Some examples using supervised learning include regression, instance-based methods, regularization methods, decision tree learning, Bayesian, kernel methods, clustering methods, association rule learning, artificial neural networks, dimensionality reduction, and ensemble methods. Probabilistic boosting tree, hierarchal, or other processes may be used.

For training, the extracted features and known ground truth for the samples of the training data are used to learn to detect, estimate, extrapolate, or image. The input feature vectors and corresponding results for many samples are used in machine learning. Tens, hundreds, or thousands of examples are used to train. Greater numbers of training examples may result in more reliable classification. The corresponding feature values are used to map the feature values to the results. Adversarial training may be used.

Rather than training one network, the network may be learned as a network of different models, where each model works on some subset or the entirety of the feature space. The outputs from each model may be used as inputs to other models, thereby creating new features. The output from one model may be used as an input to the same model to produce recursive model estimates. Feed forward or skip connections may be used in a network architecture. The network may be trained to learn from categorical, discrete, and/or continuous features. The network may be a combination of multiple interacting machine-learnt networks, each of which use the same or a different subset of features. The outputs from one model can be used as an input to another model.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for electrophysiology (EP) mapping based on electrocardiogram (ECG) and imaging hardware, the method comprising:
    detecting a three-dimensional exterior surface of a patient from a sensor;
    modeling a heart of the patient from two-dimensional x-ray images and the detected three-dimensional exterior surface of the patient, the modeling providing a three-dimensional heart mesh as a heart segmentation, wherein the three-dimensional heart mesh is formed, by an image processor applying a machine-learnt regression model trained to extrapolate three-dimensional heart surfaces from three-dimensional exteriors and a heart shadow from two-dimensional projection images, based on the detected three-dimensional exterior surface of the patient and the two-dimensional x-ray images of the patient;

measuring electric potentials at electrode locations on the patient with ECG electrodes;

generating an EP map, spatially distributed on the formed three-dimensional heart mesh, for at least a part of the heart from the detected three-dimensional exterior surface of the patient, the heart segmentation provided from the modeling, and the measured electric potentials at the electrode locations, wherein the EP map is generated from a reconstruction of a body surface potential map extrapolated from the measurements of the ECG electrodes to other locations on the detected three-dimensional exterior surface and a back projection of the body surface potential map to the formed three-dimensional heart mesh; and displaying the EP map on a display screen.

2. The method of claim 1, wherein the detecting comprises detecting the three-dimensional surface as the exterior of the patient with an optical or depth camera as the sensor.

3. The method of claim 1, wherein the modeling comprises segmenting the heart in three dimensions from the x-ray data comprising one or more two-dimensional projection representations.

4. The method of claim 1, wherein the modeling comprises forming a two-dimensional heart mask from the two-dimensional x-ray images with a deep machine-learnt neural network and forming the three-dimensional heart mesh for the heart from the two-dimensional heart mask and the detected three-dimensional exterior surface of the patient with the machine-learnt regression model.

5. The method of claim 1, further comprising localizing the ECG electrodes on the detected three-dimensional exterior surface, wherein the ECG electrodes comprises 10 or fewer ECG electrodes.

6. The method of claim 5, wherein the localizing comprises localizing with an optical or depth camera used for the detecting and a machine-learnt network, and wherein at least one of the ECG electrodes is placed on the patient at a non-standard location relative to 12-lead or 3-lead ECG.

7. The method of claim 1, wherein the generating the EP map comprises estimating heart potentials from the measured electric potentials with a mapping function from the heart segmentation to the three-dimensional exterior surface.

8. The method of claim 1, wherein the generating the EP map comprises reconstructing a body surface potential map from the measured electric potentials with a machine-learnt mapping and localized positions of the ECG electrodes, the body surface potential map having a greater density of potentials than the measured electric potentials.

9. The method of claim 1, wherein the generating the EP map comprises solving for tissue properties of the heart and determining the EP map from a virtual heart model with the tissue properties.

10. The method of claim 1 further comprising performing a sensitivity analysis using the EP map and outputting a change in position for at least one of the ECG electrodes.

11. The method of claim 1, further comprising segmenting lungs of the patient from the two-dimensional x-ray images and the three-dimensional exterior surface;

wherein generating the EP map comprises generating the EP map with an inverse mapping using the segmented lungs.

12. The method of claim 1, wherein the generating the EP map comprises generating the EP map for epicardium, endocardium, or myocardium muscle.

13. A system for electrophysiology (EP) mapping, the system comprising:

an x-ray imager configured to provide two-dimensional x-ray images;

an ECG monitor;

a red, green, blue, depth (RGBD) camera;

an image processor configured to estimate an exterior surface of a patient from the RGBD camera, estimate a three-dimensional heart mesh, by a machine-learnt regressor trained to extrapolate three-dimensional heart surfaces from three-dimensional exteriors and a heart shadow from two-dimensional projection images, from the estimated exterior surface of the patient and a heart shadow from one or more two-dimensional x-ray images of the patient output by the x-ray imager, and generate an EP map, spatially distributed on the estimated three-dimensional heart mesh, from measurements of electrodes of the ECG monitor based on the estimated exterior surface of the patient; and a display configured to display the EP map, wherein the image processor is configured to generate the EP map from a reconstruction of a body surface potential map extrapolated from the measurements of the electrodes of the ECG monitor to other locations on the detected three-dimensional exterior surface and a back projection of the body surface potential map to the estimated three-dimensional heart mesh.

14. The system of claim 13, wherein the image processor is configured to estimate the three-dimensional heart mesh based on a machine-learnt neural network configured to generate the heart shadow and the machine-learnt regressor configured to estimate the three-dimensional heart mesh from the heart shadow and the estimated exterior surface of the patient.

15. The system of claim 13 wherein the reconstruction is a function of electrode locations detected from an output of the RGBD camera.

16. The system of claim 13, wherein the x-ray imager comprises a two-dimensional x-ray system, and wherein the image processor is configured to determine a different location of at least one of the electrodes based on the EP map.

17. A system for electrophysiology (EP) mapping, the system comprising:

an image processor configured to estimate a three-dimensional exterior surface of a patient from an imager, estimate a three-dimensional heart mesh, by a machine-learnt regressor trained to extrapolate three-dimensional heart surfaces from three-dimensional exteriors and a heart shadow from two-dimensional projection images, for a heart of the patient from the estimated three-dimensional exterior surface of the patient and two-dimensional images of the patient, and generate an EP map, spatially distributed on the estimated three-dimensional heart mesh, from measurements of electric potentials on the estimated three-dimensional exterior surface of the patient by electrodes of an ECG monitor; and a display configured to display the EP map, wherein the image processor is configured to generate the EP map from a reconstruction of a body surface potential map extrapolated from the measurements of the electric potentials to other locations on the estimated three-dimensional exterior surface and a back projection of the body surface potential map to the estimated three-dimensional heart mesh.

18. The system of claim 17, wherein the image processor is configured to estimate the three-dimensional heart mesh based on a first machine-learnt network configured to generate a heart shadow from the two-dimensional images output by an x-ray scanner and the machine-learnt regressor configured to estimate the three-dimensional heart mesh from the heart shadow and the estimated three-dimensional exterior surface of the patient.

19. The system of claim 18 wherein the reconstruction is a function of electrode locations detected from an output of the imager.

* * * * *